United States Patent [19]

Kramer et al.

[11] Patent Number: 4,786,600

[45] Date of Patent: Nov. 22, 1988

[54] AUTOCATALYTIC REPLICATION OF RECOMBINANT RNA

[75] Inventors: Fred R. Kramer, Bronx; Eleanor A. Miele, Brooklyn, both of N.Y.; Donald R. Mills, Englewood, N.J.

[73] Assignee: The Trustees of Columbia University in the City of New York, New York, N.Y.

[21] Appl. No.: 614,350

[22] Filed: May 25, 1984

[51] Int. Cl.$^4$ .................. C12P 19/34; C12P 21/00; C12N 15/00; C07H 15/12
[52] U.S. Cl. .................................. 435/235; 435/6; 435/68; 435/91; 435/172.3; 435/320; 536/27; 935/2; 935/16; 935/20
[58] Field of Search ............... 435/68, 70, 172.3, 313, 435/91, 6; 536/27; 935/2, 16, 17, 20

[56] References Cited

PUBLICATIONS

Miele (1982), Ph.D. Thesis University Microfilms, Ann Arbor, Mich.
Miele et al. (1982), 11th Annual Cetus-UCLA Symp. on Gene Regulation Supp. 0(), p. 314.
Shen et al. (1982), Scientia Sinica (Ser.B.), pp. 485-495.
Nishihara et al. (1983), J. Biochem 93: 669-674.
Bsusch et al. (1983), J. Biol. Chem., 258: 1978-1984.

*Primary Examiner*—Thomas G. Wiseman
*Assistant Examiner*—S. Seidman
*Attorney, Agent, or Firm*—John P. White

[57] ABSTRACT

This invention concerns recombinant RNA molecules comprising a recognition sequence for the binding of an RNA-directed RNA polymerase, a sequence for the initiation of product strand synthesis and a heterologous sequence of interest inserted at a specific site in the internal region of the recombinant molecule. Such recombinant RNA molecules are capable of serving as a template for the synthesis of complementary single-stranded molecules by RNA-directed RNA polymerase. The product molecules so formed are also capable of serving as a template for the synthesis of additional copies of the original recombinant RNA molecule. In a preferred embodiment of the invention Q$\beta$ replicase is used as the RNA-directed RNA polymerase.

9 Claims, 3 Drawing Sheets

AUTOCATALYTIC REPLICATION OF RECOMBINANT RNA

BACKGROUND OF THE INVENTION

Throughout this application various publications are referenced by the names of the authors and the year of the publication within parentheses. Full citations for these publications may be found at the end of the specification immediately preceding the claims. The disclosures of these publications in their entireties are hereby incorporated by reference into this application in order to more fully describe the state of the art to which this invention pertains.

The synthesis of RNA in vitro by Qβ replicase (Haruna & Spiegelman, 1965a) is remarkable because a small number of template strands can initiate the synthesis of a large number of product strands (Haruna & Spiegelman, 1965b). A 100,000-fold increase in RNA can occur during a ten-minute reaction (Kramer et al., 1974). This striking amplification is the consequence of an autocatalytic reaction mechanism (Spiegelman et al., 1968; Weissmann et al., 1968). Single-stranded RNAs serve as templates for the synthesis of complementary single-stranded products. Both the product strand and the template strand are released from the replication complex and are free to serve as templates in subsequent rounds of synthesis (Dobkin et al., 1979). Consequently, the number of RNA strands increases exponentially as the reaction proceeds.

Many investigators have attempted to exploit the autocatalytic nature of Qβ replicase reactions in order to synthesize large amounts of any RNA in vitro. However, Qβ replicase does not copy most RNAs. Like other viral RNA-directed RNA polymerases it is highly selective for its own template (Haruna & Spiegelman 1965c). In vivo this enables Qβ replicase to distinguish bacteriophage Qβ RNA from the vast number of different RNA molecules that are present in *Escherichia coli*. This template specificity is a consequence of two separate interactions that occur between the replicase and Qβ RNA. First, the replicase binds strongly to a unique internal recognition sequence (Weber et al., 1974; Vollenweider et al., 1976; Meyer et al., 1981). Then, product strand synthesis is initiated at a cytidine-rich sequence located at the 3' end of the template (Rensing & August, 1969; Schwyzer et al., 1972). Each of these sequences must be present in both complementary strands for autocatalytic synthesis to occur. A number of strategies have been devised to circumvent these barriers to the synthesis of heterologous RNAs by Qβ replicase. Manganese was used to decrease the stringency of the interactions between the replicase and the template (Palmenberg & Kaesberg, 1974; Obinata et al., 1975); primers were used to bypass the normal initiation step (Feix & Hake, 1975; Feix, 1976; Vournakis et al., 1976); and polycytidine tails were added to templates to mimic the required 3'-terminal sequence (Küppers & Sumper, 1975; Owens & Diener, 1977). These strategies were tried with a wide range of heterologous templates, including rRNAs, viral RNAs and eukaryotic mRNAs. In all cases, the amount of RNA synthesized never exceeded the original amount of template RNA and the products consisted only of complementary strands. Consequently, synthesis was not autocatalytic and these methods could not approach the efficiency with which Qβ RNA is synthesized by Qβ replicase.

In a different strategy a poly (A) molecule was inserted between two Qβ RNA molecules which had been partially degraded, one from the 3'-end and another from the 5' end. *E. coli* HrH photoplasts were infected with these RNA molecules and two phage clones carrying poly (A) in their RNA were obtained after reproduction of the phage in vivo. (Tongjian and Meiyan, 1982). The yield of recombinant RNA molecules produced by this method was very low and its infectivity was between 1/1000 and 1/10000 that of the wild type RNA.

This invention concerns a method for the autocatalytic synthesis of heterologous RNAs in vitro by Qβ replicase. Our approach was to construct a recombinant RNA by inserting a heterologous sequence into a natural Qβ replicase template. The template we used, MDV-1 (+) RNA (Kacian et al., 1972), is only 221 nucleotides long, and its complete nucleotide sequence (Mills et al., 1973; Kramer & Mills, 1978) and secondary structure (Mills et al., 1980) have been determined. The mechanism of its replication by Qβ replicase has been studied in detail (Mills et al., 1978; Dobkin et al., 1979; Kramer & Mills, 1981; Bausch et al., 1983) and has been shown to be fundamentally similar to the replication of Qβ RNA. In particular, it possesses a highly structured internal binding site for Qβ replicase (Nishihara et al., 1983) and a cytidine-rich 3'-terminal sequence that is required for product strand initiation (Mills et al., 1980). We selected an insertion site at a position where the heterologous sequence would not interfere with these functional regions and where it would not disturb the structure of the MDV-1 RNA. We hoped that the replicase would respond to the recombinant RNA as it would to a natural template.

The recombinant RNA was constructed by cleaving MDV-1 (+) RNA at the selected site and then inserting decaadenylic acid in that site with the aid of bacteriophage T4 RNA ligase. This recombinant RNA was then used as a template in a reaction containing Qβ replicase. The product consisted of full-length copies of the recombinant RNA. Furthermore, both complementary strands were synthesized. The reaction proceeded autocatalytically, resulting in an exponential increase in the amount of recombinant RNA.

SUMMARY OF THE INVENTION

A recombinant single-stranded RNA molecule comprising a recognition sequence for the binding of an RNA-directed RNA polymerase, a sequence for the initiation of product strand synthesis by the polymerase and a heterologous sequence of interest derived from a different RNA molecule inserted at a specific site in the internal region of the recombinant molecule, has been synthesized.

In a specific embodiment of the invention this recombinant RNA molecule is capable of serving as a template for the synthesis of a complementary single-stranded RNA molecule by an RNA-directed RNA polymerase. The product of this synthesis is also capable of serving as a template for the synthesis of additional copies of the original recombinant RNA molecule by the polymerase.

In specific embodiments of the invention the recognition sequence for the binding of an RNA directed RNA polymerase is in the internal region of the molecule.

The specific insertion site for the heterologous RNA sequence of interest which is derived from a different molecule is not near the binding sequence of the polymerase or the sequence for the initiation of product strand synthesis. In a preferred embodiment of the invention the insertion site is at a specific nucleotide in a region where the inserted sequence has a minimal effect upon the structure of the template RNA molecule.

In a preferred embodiment of the invention the RNA template molecule is midivariant RNA (MDV-1 RNA) which serves as a template for Qβ replicase. A specific heterologous RNA sequence of interest is inserted at a site where the insertion would not significantly effect the replicability of the resulting combinant, e.g. between nucleotides 63 and 64 of MDV-1 (+) RNA.

The present invention also concerns a novel method of cleaving an RNA molecule at a specific site. According to the invention a modified cDNA molecule is hybridized to the RNA molecule to be cleaved. The non-complementary loop of the heteroduplex is cleaved by a ribonuclease at a specific nucleotide to yield the desired fragments. The invention also concerns methods of constructing recombinant RNA molecules from such fragrants and methods of synthesizing such recombinant RNA molecules in vitro.

Recombinant RNAs constructed by this method are useful as hybridization probes, since they can be highly labeled during synthesis, and since blotting with RNA instead of DNA results in lower backgrounds. Recombinants can also be made from unprocessed gene transcripts to provide a ready source of substrates for the isolation of processing enzymes and for use in studies probing RNA splicing mechanisms. Recombinants can also be made from eucaryotic messenger RNAs that are difficult to obtain. They can serve as a virtually unlimited source of mRNAs for use as templates in cell-free translation systems. Thus, recombinant mRNAs may provide a novel means for obtaining useful quantities of rare proteins. Recombinant RNAs also provide a means for directly sequencing the heterologous insert by replication in the presence of 3'-deoxyribonucleoside 5'-triphosphate chain terminators. Furthermore, recombinant RNAs can be constructed from the genomes of viruses and viroids. Mutants of these recombinants can then be selected through the use of in vitro evolution techniques that have been developed for Qβ RNA. The mutant heterologous sequences can be recovered from the recombinants and can then be introduced into cells to study their altered biological activity. In summary, the autocatalytic replication of recombinant ribonucleic acids constructed from genomes and gene transcripts provides a powerful tool for probing and manipulating genetic information.

BRIEF DESCRIPTION OF THE FIGURES

FIG. 1. Secondary structure of MDV-1 (+) RNA, showing the site at which decaadenylic acid was inserted into the sequence (indicated by an arrow). Bold letters identify those nucleotides that are found in homologous regions of Qβ (−) RNA (Nishihara et al., 1983). Of 46 nucleotides between positions 81 and 126, 40 are identical with nucleotides 84 to 129 of Qβ (−) RNA and 30 of 35 nucleotides between positions 187 and 221 are identical with nucleotides 4186 to 4220 at the 3' end of Qβ (−) RNA. These regions contain major elements of the internal replicase binding site and the product strand initiation site.

FIG. 2. Heteroduplex formed by the hybridization of MDV-1 (+) RNA to modified MDV-1 (−) cDNA. The arrow indicates the site at which ribonuclease T₁ cleaved the RNA strand into 2 fragments. Sequence hyphens have been omitted for clarity.

FIG. 4. Comparison of the kinetics of MDV-1 RNA synthesis and recombinant RNA synthesis. The logarithm of the amount of RNA present in each sample was plotted as a function of incubation time. The amount of RNA in each reaction increased exponentially, until the number of RNA strands equaled the number of active replicase molecules, and thereafter increased linearly.

DETAILED DESCRIPTION OF THE INVENTION

A recombinant single-stranded RNA molecule comprising a recognition sequence for the binding of an RNA-directed RNA polymerase, a sequence for the initiation of product strand synthesis by the polymerase and a heterologous sequence of interest derived from a different RNA molecule inserted at a specific site in the internal region of the recombinant molecule has been synthesized.

The recombinant RNA molecule is capable of serving as a template in vitro for the synthesis of a complmentary single-stranded RNA molecule by an RNA-directed RNA-polymerase. This complementary product molecule is also capable of serving as a template in vitro for the synthesis of additional copies of the original recombinant molecule by the RNA-directed RNA polymerase.

The recognition sequence on the recombinant molecule for the binding of the RNA-directed RNA-polymerase is located in an internal region of the molecule. In preferred embodiments of the invention the insertion site for the heterologous RNA sequence of interest is not located near any surface required for the binding of the RNA polymerase or for the initiation of product strand synthesis, in order not to interfere with the template activity of the recombinant RNA molecule. It is also desirable to locate this insert in a position in the molecule were its effect upon the secondary structure of the molecule, and thus its template activity, will be minimal.

In a specific embodiment of the invention the sequence required for the initiation of product strand synthesis is a cytidine rich sequence located on the 3' terminal end of the molecule.

In another embodiment, the recombinant RNA molecule contains at least one radiolabeled nucleotide. In a preferred embodiment, the nucleotide contains numerous radiolabeled nucleotides.

In a specific embodiment of the invention the RNA-directed RNA polymerase is Qβ replicase. The recombinant RNA molecules in this embodiment contain a template for Qβ replicase and a heterologous RNA sequence of interest derived from a different RNA molecule inserted, as in other embodiments, at a specific site in the template, e.g., at or near a specific nucleotide.

The Qβ replicase template can be variant RNA, e.g., midivariant RNA, minivariant RNA, microvariant RNA, one of the nanovariant RNAs, other variants to which names have not yet been assigned, or mutants thereof. It is preferred that the insertion site of the heterologous RNA sequence of interest be located in a region where the sequences are not known to be required for replication, e.g., in a loop where viable mutations are known to occur, and is preferably on the exterior of the molecules, e.g., at or near a guanosine residue which is hypersusceptible to cleavage by ribonuclease $T_1$.

In a specific embodiment of the invention the template is MDV-1 RNA or a mutant thereof. Either the MDV-1 (+) RNA or MDV-1 (−) RNA molecules may be used.

In a presently preferred embodiment the heterologous RNA sequence of interest is inserted, e.g., between nucleotides 63 and 64 of the MDV-1 (+) RNA molecule. The heterologous RNA sequence may be, e.g. a natural or synthetic mRNA, a primary gene transcript or a transcript obtained by in vitro transcription from recombinant DNA or genomic RNA. In a specific embodiment of the invention, the heterologous sequence is decaadenylic acid and it is inserted between nucleotides 63 and 64 of the MDV-1 (+) RNA molecule.

The invention also concerns single-stranded RNA and DNA molecules which are complementary to the single-stranded RNA template. These complementary molecules can be prepared by any conventional method, e.g. by enzymatic or chemical synthesis.

In one embodiment, a molecule complementary to the Qβ replicase template molecule may be prepared. An MDV-1 (−) cDNA molecule was thus prepared enzymatically by reverse transcriptase from MDV-1 (+) RNA. This molecule and other cDNA molecules of this invention can be cloned as an insert in a DNA-vector such as a plasmid, e.g. pBR322.

Another aspect of this invention concerns modified single-stranded cDNA molecules useful in a method for cleaving an RNA molecule at a specific site. In one embodiment, the modified cDNA molecule is modified in that a segment of the DNA molecule is replaced with a non-homologous segment, of DNA. The DNA segment replaced is the segment of the cDNA molecule which is complementary to the nucleotide sequence of a desired specific cleavage site on the RNA molecule. The non-homologous replacement segment is not capable of hybridizing to the nucleotides of the specific cleavage site. The non-homologous replacement may contain a different number of nucleotides than the RNA cleavage site. In one embodiment the DNA replacement segment contains eight nucleotides and the RNA cleavage site contains three nucleotides. This non-homologous segment can be the cleavage site of a restriction enzyme, e.g. endonuclease XbaI. The modifications may be performed enzymatically or chemically. In this and other embodiments the RNA may be a template for an RNA-directed RNA polymerase, e.g., Qβ replicase. Where the polymerase is Qβ replicase the template may be midivariant RNA.

In a specific embodiment of the invention a modified cDNA molecule is substantially complementary to MDV-1 (+) RNA and contains a modification in the region complementary to the specific cleavage site of the MDV-1 (+) RNA between nucleotides 63 and 64. The MDV-1 (−) cDNA modification comprises the replacement the 3 base pair DNA segment complementary to RNA nucleotides 62 to 64 with an 8 nucleotide non-homologous segment. In one embodiment the non-homologous segment is C—T—C—T—A—G—A—G, which contains the XbaI site.

Modified cDNA molecules prepared according to this invention may be obtained in large quantities by inserting them into a vector DNA molecule, e.g. plasmid pBR322, and producing them in large quantities in host cells, e.g. *E. coli.*

The modified cDNA molecules so produced are useful in methods of cleaving a single-stranded RNA molecule at specific sites. A modifed cDNA molecule substantially complementary to the RNA molecule to be cleaved as described above, e.g. an MDV-1 (+) RNA molecule and a substantially complementary MDV-1 (−) cDNA molecule, is incubated with the RNA molecule to be cleaved under suitable conditions and for a sufficient period of time permitting the hybridization of substantially complementary molecules. The heteroduplex formed is isolated upon completion of hybridization and contains a non-hybridized loop at the region where the strands are not complementary. The RNA strand of the heteroduplex is then cleaved in the region of the non-complementary loop, e.g. between nucleotides 63 and 64 of MDV-1 (+) RNA. Site-specific cleavage of the RNA may be effected by a variety of means including chemical and enzymatic reactions. Presently preferred, however, is the use of a ribonuclease, e.g. ribonuclease $T_1$ to cleave the RNA. The cleaved heteroduplex may be isolated and separated, e.g. by melting to obtain single-stranded RNA and DNA molecules. The RNA fragments so obtained are separated and purified, to yield in one embodiment using ribonuclease $T_1$, a 63 nucleotide MDV-1 (+) RNA fragment with a natural 5′ terminal triphosphate and a 158 nucleotide MDV-1 (+) RNA fragment with a natural 3′ terminal hydroxyl group.

Fragments of RNA molecules which are useful as templates for the synthesis of RNA by an RNA-directed RNA polymerase can be obtained by these specific cleavage methods. Since these fragments have been cleaved at a specific known cleavage site they are useful as components of recombinant RNA molecules.

The present invention also concerns methods for the construction of recombinant RNA molecules from the RNA template fragments obtained by site specific cleavage. A 5′ terminal phosphate is added to the fragment that acquired a 5′ terminal hydroxyl group as a result of the cleavage by ribonuclease $T_1$, e.g. the 158 nucleotide MDV-1 (+) RNA fragment. A heterologous RNA sequence of interest derived from a different molecule, e.g. decaadenylic acid, is ligated to the 5′ terminus of the phosphorylated fragment. The ligation can be by chemical or enzymatic methods, but it is preferably performed enzymatically with bacteriophage $T_4$ RNA ligase. After the ligation is completed a 5′ terminal phosphate is added to the ligated product, e.g. the 168 nucleotide MDV-1 (+) RNA fragment containing decaadenylic acid. The terminal phosphates are then removed from the fragment which acquired a 3′ terminal phosphate as a result of the cleavage by ribonuclease T1, e.g. the 63 nucleotide MDV-1 (+) RNA fragment. This dephosphorylated fragment is then ligated to the product of the previous ligation and the resulting recombinant RNA molecule is isolated and purified.

In a preferred embodiment of the invention MDV-1 (+) RNA is used as the vector for the construction of a recombinant RNA molecule. The use of this natural Qβ replicase template, should allow for the introduction of large heterologous RNA sequences into the recombinant molecules. This should be possible since the natural substrate for Qβ replicase, Qβ RNA, is approximately 4200 nucleotides in length, whereas MDV-1 RNA is 221 nucleotides in length. Any type of heterologous single-stranded RNA molecule, from any origin may be an insert in the recombinant RNA molecules of this invention.

The invention also concerns in vitro methods of synthesizing the recombinant RNA molecules so constructed. The recombinant RNA molecules are incubated with the RNA-directed RNA polymerase for which they serve as a template under suitable conditions permitting RNA replication. Large amounts of the recombinant RNA molecules can thus be obtained.

In a specific embodiment of the invention MDV-1 (+) recombinant RNA containing an insert between nucleotides 63 and 64 is incubated with Qβ replicase. These recombinant molecules are capable of autocatalytic replication wherein the complementary product strand produced also serves as a template for synthesis of the recombinant RNA the Qβ replicase.

Another embodiment of the invention concerns a method of specifically cleaving the MDV-1 (+) RNA recombinant molecule which contains the decaadenylic sequence. Cleavage by this method results in fragments of the MDV-1 (+) RNA molecule in which the phosphate and hydroxyl residues are in correct orientation for the ligation of another heterologous RNA sequence of interest. The recombinant MDV-1 (+) RNA molecule containing the decaadenylic acid sequence is incubated with decathymidylic acid under suitable conditions permitting the hybridization of complementary strands. The hybrid so formed is treated with ribonuclease H under suitable conditions permitting the digestion of the decaadenylate insert. The RNA fragments obtained are then separated and isolated. This method of cleavage results in an MDV-1 (+) RNA fragment of about 63 nucleotides containing a 3′ terminal hydroxyl group and an MDV-1 (+) RNA fragment of about 158 nucleotides containing a 5′ terminal phosphate group. These fragments can then be used in a ligation reaction with other heterologous RNA sequences of interest to construct other MDV-1 (+) RNA recombinant molecules capable of autocatalytic replication.

In a specific embodiment of the invention the recombinant RNA molecules can be used to sequence a specific nucleic acid sequence of interest. The nucleic acid sequence of interest is present as a heterologous RNA insert at a specific site of the recombinant molecule. The recombinant molecule is autocatalytically replicated in vitro by Qβ replicase in the presence of 3′ deoxyribonucleoside 5′-triphosphate chain terminators. The RNA molecules of various length so obtained are then analyzed by standard molecular biology sequencing techniques.

Recombinant RNA molecules constructed from appropriate sequences are also useful as hybridization probes in a method for determining the presence or concentration of an oligo- or polynucleotide, e.g. DNA, of interest in a mixture. Suitable recombinant RNA molecules may be obtained by preparing an RNA molecule complementary to the oligo- or polynucleotide of interest by methods known in the art. Using the complementary RNA strand so obtained as a heterologous segment of a recombinant RNA molecule of this invention permits the convenient autocatalytic synthesis of recombinant RNA molecules useful as hybridization probes for the material of interest. Recombinant RNA molecules of this invention are particularly advantageous in such methods because they can be densely labeled with radiolabeled nucleotides and since blotting with RNA instead of DNA results in lower backgrounds. According to one method of this invention a radiolabeled recombinant RNA molecule or derivative thereof is contacted with a mixture under suitable conditions and for a sufficient period of time permitting complementary nucleotide segments to hybridize. The recombinant RNA molecule or fragment thereof contains a nucleotide segment complementary to the oligo- or polynucleotide of interest. The presence or intensity of radioactivity in hybridized nucleotide segments is then determined and correlated with the presence or concentration of the oligo- or polynucleotide of interest.

This method is widely applicable for use in any of the available configurations useful for DNA hybridization probes. It may be used in a diagnostic device or kit for the detection of nucleotide segments associated with a disorder in plants or animals, including humans.

In another embodiment of the invention a recombinant RNA molecule may be used as a hybridization label in a method for labeling an oligo- or polynucleotide of interest in biological material, e.g., a tissue sample. The recombinant RNA or a derivative thereof contains at least one, and preferably more than one, radiolabeled nucleotide. The RNA or RNA fragment also contains a nucleotide segment complementary to the oligo- or polynucleotide of interest. The method involves contacting the radiolabeled RNA or RNA derivative with the biological material under suitable conditions and for a sufficient period of time to permit complementary nucleotide segments to hybridize. Hybridization according to this method effectively radiolabels the oligo- or polynucleotide of interest.

In a further embodiment, the recombinant RNA molecules or derivatives thereof may be used in a cell-free method of protein synthesis. The recombinant RNA useful in this method is prepared by the method disclosed above and contains a heterologous nucleotide sequence coding for a desired protein. The RNA itself may be used in this method. Alternatively, the heterologous sequence may be cleaved from the template molecule after replication and used in place of the complete recombinant molecule. In either case, the heterologous sequence may also contain additional nucleotide sequences, e.g., one or more introns, a 5′ cap or polyadenylic acid tail, and may be further derivatized, e.g. methylated. In accordance with this method, a mixture is prepared containing the RNA or RNA-derivative coding for the desired protein, a cellular extract capable of synthesizing a protein encoded by the recombinant RNA or derivative, and an effective amount of appropriate amino acids and buffer. The cellular extract may be obtained from bacterial cells, or from eucaryotic cells, e.g. rabbit reticulocytes or wheat germ, and contains ribosomes and various soluble enzymes. The mixture is incubated under suitable conditions permitting enzymatic synthesis of the encoded protein. By this method rare proteins and proteins of significant scientific, medical or commercial utility may be conveniently obtained in small scale reactions as well as on an industrial scale.

In another embodiment, the recombinant RNA molecules of this invention may be used in a method for identifying or characterizing an RNA processing enzyme in a biological material. According to this method a recombinant RNA molecule is prepared by the methods disclosed above and contains a heterologous sequence comprising a primary gene transcript. The primary gene transcript is a substrate for the RNA processing enzyme of interest. The RNA molecule or a derivative thereof which also comprises a substrate for the enzyme of interest is incubated with the biological material under suitable conditions permitting an RNA processing enzyme to cleave a substrate RNA molecule. By detecting the presence of character of RNA cleavage products it is possible to identify or characterize the enzyme. In a specific embodiment, the RNA molecule is a transcript of a recombinant DNA molecule, the transcript comprising a substrate of the enzyme of interest.

In a further embodiment, a recombinant RNA molecule of this invention may be used in a method for producing a mutant virus or viroid. The recombinant RNA molecule contains a heterologous inserted sequence comprising the RNA genomes of the virus or viroid of interest. Incubating the recombinant molecule under appropriate selective conditions and for a sufficient period of time permits the accumulation, i.e., the selection, of a population of mutant replicates. Suitable selective conditions are numerous and varied, but include replicating the recombinant molecules in the presence of a chain elongation inhibitor, e.g. ethidium bromide; a nuclease, e.g., ribonuclease $T_1$; or a chain terminator, e.g., cordycepin 5'-triphosphate. Mutant viruses or viroids so obtained may be useful in exploring the role of different nucleotide sequences in pathogenicity, infectivity and replicability. Furthermore, mutants of reduced pathogenicity may be obtained by this method which may be protect plant or animal from infection by a more pathogenic form.

In still another embodiment of this invention the recombinant RNA molecules may be used in a method for isolating one type of RNA from a mixture of different RNA molecules. The method involves preparing a mixture of recombinant RNA molecules according to the methods described herein. The heterologous fragments incorporated into the template RNA molecules to form the recombinant molecules comprise the mixture of RNA molecules containing the RNA of interest. The mixture of recombinant RNA molecules is serially diluted until convenient aliquots may be withdrawn from the mixture, each of which containing one molecule of recombinant on average. Each aliquot is then separately incubated with an appropriate RNA-directed RNA polymerase under suitable conditions permitting autocatalytic synthesis of copies of the recombinant RNA. Homogeneous populations of recombinant copies are then identified. The homogeneous populations so identified are screened for populations containing copies of the recombinant molecule containing the RNA of interest.

The following experimental procedures are set forth to illustrate specific embodiments of the invention. While these embodiments utilize midivariant RNA, this invention contemplates the use of other RNA templates for other RNA-directed RNA polymerases. Furthermore, the invention contemplates the use of any heterologous RNA segment which may be inserted in such RNA templates at various specific template sites.

MATERIALS AND METHODS (a) Materials $Q\beta$ replicase was isolated from bacteriophage $Q\beta$-infected E. coli Q13, using the procedure of Eoyang & August (1971) with the hydroxylapatite-chromatography step omitted. The following enzymes were purchased: bacteriophage $T_4$ RNA ligase from P-L Biochemicals, Milwaukee, WI; bacteriophage $T_4$ polynucleotide kinase from Boehringer-Mannheim Biochemicals, Indianapolis, IN; bacterial alkaline phosphates and restriction endonuclease EcoRI from Bethesda Research Laboratories, Bethesda, Md.; proteinase K from EM laboratories, Elmsford, N.Y.; and ribonuclease $T_1$ from Calbiochem, La Jolla, Calif. Decaadenylic acid (lacking terminal phosphates) was obtained from P-L Biochemicals. Radioactive ribonucleoside 5'-triphosphates were purchased from ICN, Irvine, Calif., and unlabeled ribonucleoside 5'-triphosphates were obtained from P-L Biochemicals.

(b) MDV-1 (+) RNA

The synthesis of MDV-1 RNA (Kramer et al., 1974) and the isolation of the complementary (+) and (−) strands by polyacrylamide slab gel electrophoresis in the presence of magnesium ions (Mills et al., 1978) have been described. A mutant MDV-1 RNA was used in these studies. Its nucleotide sequence differed from the wild-type sequence at position 61 of the (+) strand, where there was an adenosine in place of a guanosine residue (Kramer et al., unpublished results).

(c) Modified MDV-1 cDNA

The synthesis of MDV-1 cDNA by avian myeloblastosis virus reverse transcriptase, its cloning into the EcoRI site of pBR322 DNA, and the modification of its nucleotide sequence in the region of its unique HinfI site have been described (Bausch et al., 1983). The modification involved the replacement of a 3 base-pair segment (nucleotides 62 to 64 in the MDV-1 (+) strand and nucleotides 157 to 159 in the (−) strand) with an 8 base-pair segment containing an XbaI site (C—T—C—T—A—G—A—G in each strand). Modified MDV-1 cDNA was isolated from the plasmid by digestion with endonuclease EcoRI.

(d) Site-directed cleavage of MDV-1 (+) RNA

MDV-1 (+) RNA was hybridized to MDV-1 (−) cDNA in an aqueous formamide solution (Casey & Davidson, 1977) as follows: 34 μg of [α-$^{32}$P]GTP-labeled MDV-1 (+) RNA and 68 μg of modified MDV-1 cDNA were incubated in 50 μl of 800 mg. formamide/ml, 300 mM NaCl, 30 mM sodium citrate (pH 6.5) at 80° C. for 10 min to melt the double-stranded DNA. This solution was then incubated at 55° C. for 24 h to promote annealing. Then 100 μl of standard buffer (20 mM Tris-HCl (pH 7.5), 400 mM NaCl, 3mM EDTA, 1 mg sodium dodecyl sulfate/ml) was added, and the MDV-1 (+) RNA/MDV-1 (−) cDNA heteroduplex was isolated from the mixture by gel filtration chromatography on Sepharose 4B eluted in standard buffer. The hybrid was then precipitated with 2 vol. ethanol.

The MDV-1 (+) RNA in the heteroduplex was cleaved between nucleotides 63 and 64 by incubating 48 μg of the hybrid at 0° C. for 60 min in 3 ml of 100 units of ribonuclease $T_1$/ml, 100 mM Tris-HCl (pH 7.4), 20 mM $MgCl_2$. The volume was brought to 6 ml with the addition of proteinase K to 50 μg/ml, sodium dodecyl sulfate to 5 mg/ml, Tris-HCl (pH 7.4) to 100 mM, NaCl to 400 mM, and EDTA to 30 mM. This solution was incubated at 23° C. for 60 min to destroy the ribonuclease. Protein was then extracted twice with an equal volume of water-saturated phenol and the nicked heteroduplex was precipitated with 2 vol. ethanol. The cleaved heteroduplex was melted apart in 7M urea at 100° C., and the RNA fragments were separated electrophoretically (Mills & Kramer, 1979) and eluted from the gel. The length and identity of each fragment was confirmed by nucleotide sequence analysis (Sanger et al., 1965).

(e) Construction of the recombinant RNA

A 5'-terminal phosphate was added to the 158-nucleotide fragment of the cleaved MDV-1 (+) RNA according to the method of Donis-Keller et al. (1977): 6 µg of the fragment were incubated at 50° C. for 3 min in 140 µl of 1mM spermidine, 10 mM Tris-HCl (pH 7.4), 100 M EDTA, and then rapidly chilled to 0° C. The volume was brought to 200 µl with the addition of bacteriophage $T_4$ polynucleotide kinase to 225 units/ml, [$\gamma$-$^{32}$P]adenosine 5'-triphosphate to 3 µM, Tris-HCl (pH 7.4) to 50 mM, $MgCl_2$ to 10 mM, and dithiothreitol to 5 mM. This solution was incubated at 37° C. for 2 h. The reaction was terminated by the addition of 200 µl of standard buffer. Protein was extracted with an equal volume of phenol and the phosphorylated fragment was precipitated with 2 vol. ethanol.

Decaadenylic acid (lacking terminal phosphates) was ligated to the 5' end of the phosphorylated 158-nucleotide fragment as follows: the decaadenylic acid, which was purchased as an ammonium salt, was converted to a sodium salt by dissolving it in 400 mM NaCl and precipitating it with 2 vol. ethanol. Sodium decaadenylic acid (50 nmol) and 4 µg of phosphorylated 158-nucleotide fragment were incubated at 50° C. for 3 min in 70 µl of 1 mM spermidine, 10 mM Tris-HCl (pH 7.4), 100 µM EDTA, and then rapidly chilled to 0° C. The volume was brought to 100 µl with the addition of bacteriophage $T_4$ RNA ligase to 400 units/ml, Tris-HCl (pH 7.4) to 50 mM, $MgCl_2$ to 10 mM, and dithiothreitol to 5 mM. This solution was incubated at 4° C. for 30 h. The reaction was terminated by the addition of 100 µl of standard buffer. Protein was extracted with an equal volume of water-saturated phenol and the RNA was precipitated with 2 vol. ethanol. The RNA was then separated by polyacrylamide gel electrophoresis and the 168-nucleotide ligation product was eluted from the gel.

A 5'-terminal phosphate was added to the 168-nucleotide ligation product as follows: 1 µg of the 168-nucleotide product was incubated at 37° C. for 2 h in 20 µl of 225 units $T_4$ polynucleotide kinase/ml, 2 µM-[$\gamma$-$^{32}$P]adenosine 5'-triphosphate, 50 mM Tris—HCl (pH 7.4), 10 mM $MgCl_2$, 5 mM dithiothreitol. The reaction was terminated by the addition of 80 µl of standard buffer. Protein was extracted with an equal volume of water-saturated phenol and the RNA was precipitated with 2 vol. ethanol. The phosphorylated 168-nucleotide product was then purified further by polyacrylamide gel electrophoresis.

The terminal phosphates of the 63-nucleotide fragment of the cleaved MDV-1 (+) RNA were removed as follows: 2 µg of the fragment were incubated at 37° C. for 2 h in 100 µl of 14 units of bacterial alkaline phosphatase/µl, 100 mM Tris-HCl (pH 8.3), 20 mM $MgCl_2$. The reaction was terminated by the addition of 100 l of 100 mM EDTA, 800 mM NaCl, 10 mg sodium dodecyl sulfate/ml. Protein was extracted with an equal volume of water-saturated phenol and the dephosphorylated fragment was precipitated with 2 vol. ethanol.

The dephosphorylated 63-nucleotide fragment was ligated to the 5' end of the phosphorylated 168-nucleotide product as follows: 2 µg of the dephosphorylated 63-nucleotide fragment and 100 ng of the phosphorylated 168-nucleotide product were incubated at 37° C. for 2 h in 10 µl of 400 units of $T_4$ RNA ligase/ml, 50 mM Tris-HCl (pH 7.4), 10 mM $MgCl_2$, mM dithiothreitol. The reaction volume was then doubled by the addition of fresh buffer and ligase, and incubation was continued at 4° C. for 48 h. The reaction was terminated by the addition of 80 µl of standard buffer. Protein was extracted with an equal volume of water-saturated phenol and the RNA was precipitated with 2 vol. ethanol. The RNA was then separated by polyacrylamide gel electrophoresis: 310 pg of the 231-nucleotide recombinant RNA were recovered from the gel.

(f) Replication of the recombinant RNA

The synthesis of recombinant RNA by $Q\beta$ replicase was carried out according to the protocol of Kramer et al. (1974). Recombinant template RNA (100 pg) was incubated for 15 min in a 12.5 µl reaction volume. The product RNA was electrophoretically purified, melted in 7M urea at 100° C. and the complementary (+) and (−) strands were separated (Mills et al., 1978). The identity of each of the complementary recombinant RNA strands was confirmed by nucleotide sequence analysis.

(g) Kinetic analysis of recombinant RNA synthesis

Recombinant (−) RNA (392 pg) was incubated at 37° C. in 75 µl of 20 µg $Q\beta$ replicase/ml, 84 mM Tris—HCl (pH 7.4), 12 mM $MgCl_2$, 200 µM ATP, 200 µM CTP, 200 µM UTP and 250 µM [$\alpha$-$^{32}$P]GTP. A control reaction was also prepared, in which 375 pg of MDV-1 (−) RNA was used as template. Samples (5 µl) were taken from each reaction at 1 min intervals and immediately diluted with 200 µl of standard buffer containing 10 µg of unlabeled yeast RNA as carrier. The protein in each sample was extracted with an equal volume of phenol and the RNA in 100 µl of each aqueous phase was precipitated with 2 vol. ethanol. The RNA samples were then analyzed, in parallel, by polyacrylamide gel electrophoresis. Their homogeneity was confirmed by an examination of the autoradiograph. The amount of RNA in each gel band was determined by scintillation counting. These data were used to compare the rate of recombinant RNA synthesis with the rate of MDV-1 RNA synthesis.

RESULTS (a) Selection of the insertion site

Figure 1:
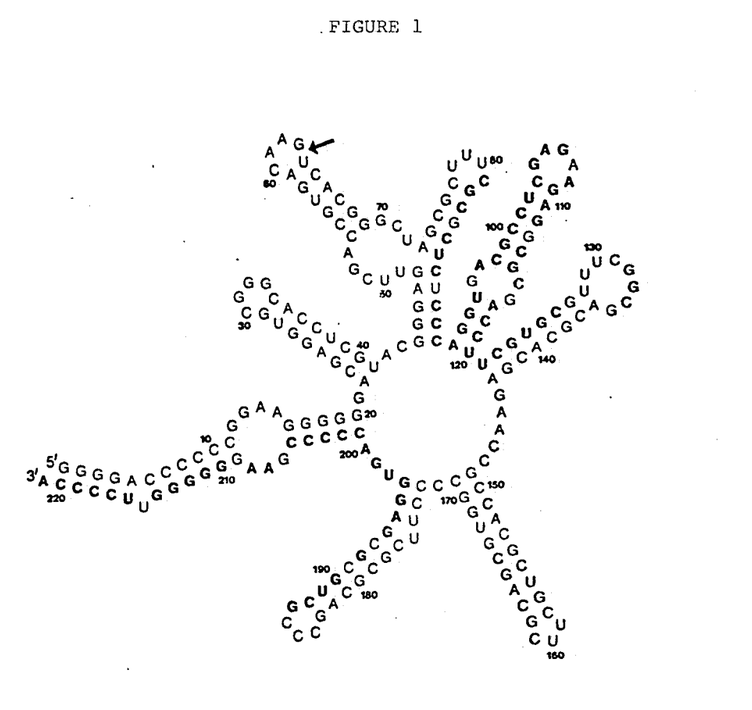

Autocatalytic replication of a recombinant RNA cannot occur if the addition of the heterologous sequence to the $Q\beta$ replicase template interferes with normal template function. We therefore chose an insertion site in MDV-1 (+) RNA that was not near any sequence known to be required for replication. In addition, the selected insertion site was in a region where the presence of a heterologous sequence would have a minimal effect on template structure. FIG. 1 shows the secondary structure of MDV-1 (+) RNA predicated by computer analysis (Zuker & Stiegler, 1981) and established by chemical modification (Mills et al., 1980), observation of band compression regions in sequencing gels (Kramer & Mills, 1978; Mills & Kramer, 1979), and structure mapping with ribonuclease $T_1$ (Kramer et al., 1981). Two regions of MDV-1 (+) RNA that are homologous with regions of Qβ (−) RNA are shown in the Figure. One is the highly structured internal region that contains major elements of the template recognition site (Nishihara et al., 1983). The other is the cytidine-rich 3'-terminal sequence required for product strand initiation (Mills et al., 1980). The insertion site that we selected was located away from these regions, between nucleotides 63 and 64.

There are additional reasons why this particular site was chosen. Computer analysis indicated that the ends of the fragments generated by cleavage at the site were likely to be single-stranded, which would facilitate their subsequent ligation (England & Uhlenbeck, 1978). The site was located in a hairpin loop, where it was least likely to disturb the structure. Viable mutations were known to occur in this hairpin loop (Kramer et al., unpublished results), suggesting that its sequence was not essential for replication. And finally, the site was probably on the exterior of the molecule, because the guanosine residue in the hairpin loop is hypersusceptible to cleavage by ribonuclease $T_1$ (Kramer et al., unpublished results).

(b) Site-directed cleavage

Figure 2:
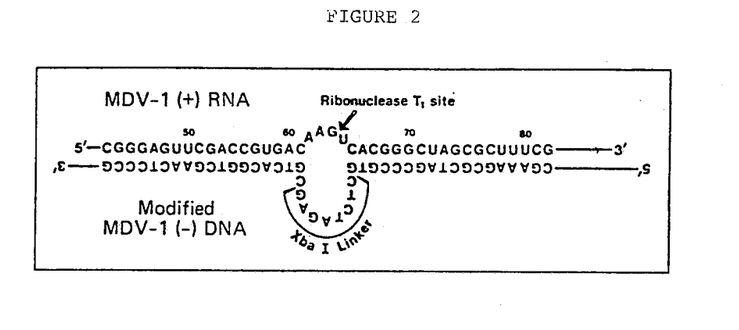

To cleave MDV-1 (+) RNA between nucleotides 63 and 64, a heteroduplex was formed between [α-$^{32}$P]GTP-labeled MDV-1 (+) RNA and modified MDV-1 (−) cDNA. The modified MDV-1 (−) cDNA contained an eight-nucleotide sequence, C—T—C—T—A—G—A—G, in place of the sequence that is complementary to nucleotides 62 to 64 of the (+) strand (Bausch et al., 1983). Consequently, the RNA in the heteroduplex was completely hybridized to the DNA except in the region of the modified sequence (see FIG. 2). The heteroduplex was then digested with ribonuclease $T_1$. Since ribonuclease $T_1$ cleave RNA only on the 3' side of guanosine residues in single-stranded regions (Sato-Asano, 1959), the modified cDNA served as a mask, limiting cleavage to the 3' phosphodiester bond of the lone exposed guanosine residue at position 63. The cleaved heteroduplex was isolated from the digestion mixture, melted apart, and the two RNA fragments were separated from each other by polyacrylamide gel electrophoresis. Each fragment was eluted from the gel and its length and homogeneity were confirmed by nucleotide sequence analysis. The 63-nucleotide fragment possessed a natural 5'-terminal triphosphate and acquired a 3'-terminal phosphate as a consequence of cleavage. The 158-nucleotide fragment acquired a 5'-terminal hydroxyl group as a consequence of the cleavage and possessed a natural 3'-terminal hydroxyl group.

(c) Construction of the recombinant RNA

Figure 3:
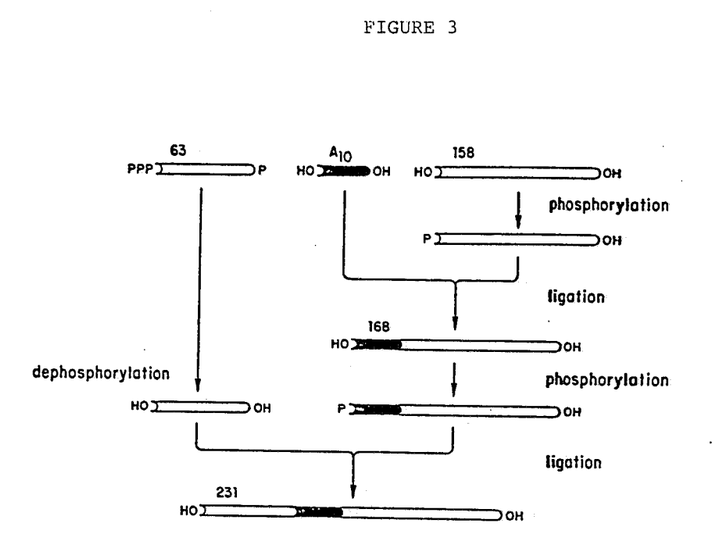
FIG. 3. Construction of a recombinant RNA: (1) a phosphate was added to the 5' end of the 158-nucleotide fragment of MDV-1 (+) RNA; (2) decaadenylic acid (lacking terminal phosphates) was ligated to the phosphorylated 158-nucleotide fragment, forming a 168-nucleotide fragment: (3) a phosphate was added to the 5' end of the 168-nucleotide fragment: (4) the 63-nucleotide fragment of MDV-1 (+) RNA was dephosphorylated; and (5) the dephosphorylated 63-nucleotide fragment was ligated to the phosphorylated 168-nucleotide fragment, forming a 231-nucleotide recombinant RNA.

The insertion of decaadenylic acid between the two MDV-1 (+) RNA fragments was accomplished in two stages with the aid of bacteriophage $T_4$ RNA ligase (Silber et al., 1972), utilizing methods developed by Kaufmann & Littauer (1974) and Uhlenbeck & Cameron (1977). First, the decaadenylic acid was ligated to the 5' end of the 158-nucleotide fragment, forming a 168-nucleotide fragment. Then, the 63-nucleotide fragment was ligated to the 5' end of the 168-nucleotide fragment, forming a 231-nucleotide recombinant RNA. Since $T_4$ RNA ligase requires a 3'-hydroxyl group on the fragment containing the reactive 3' end and a 5' phosphate on the fragment containing the reactive 5' end (Kaufmann & Kallenbach, 1975; Walker et al., 1975), preliminary reactions were carried out to convert the ends of each fragment to the appropriate form. FIG. 3 summarizes the steps required to construct the recombinant RNA.

The 5' end of the 158-nucleotide fragment was phosphorylated by bacteriophage $T_4$ polynucleotide kinase, in a reaction that utilized [α-$^{32}$P]ATP. Decaadenylic acid, which lacked terminal phosphates, was then added to the 5' end of the phosphorylated 158-nucleotide fragment with the aid of $T_4$ RNA ligase. There were 624 times as many moles of decaadenylic acid present in the reaction as there were moles of 158-nucleotide fragment. The presence of a large excess of the non-phosphorylated fragment increased the rate of ligation and minimized the undesirable dimerization of the phosphorylated fragment (Walker et al., 1975). The 168-nucleotide ligation product was isolated by polyacrylamide gel electrophoresis. Analysis of the gel indicated that 60% of the 158-nucleotide fragments had been ligated to decaadenylic acid. Each synthetic step was monitored by nucleotide sequence analysis. Before phosphorylation, the 5' end of the 158-nucleotide fragment yielded a unique oligonucleotide, U—C—A—C—G. After the addition of a 5'-terminal phosphate (of a much higher specific radioactivity than was used to label the internal phosphates), the 5' end of the 158-nucleotide fragment was seen as pU—C—A—C—G, which migrates to a different position in the fingerprint pattern that U—C—A—C—G. The ligation of decaadenylic acid to the 5' end of the phosphorylated 158-nucleotide fragment resulted in the disappearance of pU—C—A—C—G and the appearance of a highly labeled oligonucleotide that migrated to a position in the fingerprint pattern (Sanger et al., 1965) that identified it as the expected $(A)_{10}$U—C—A—C—G.

In preparation for the next ligation, the 5' end of the 168-nucleotide ligation product was phosphorylated by $T_4$ polynucleotide kinase in a reaction that utilized [γ-$^{32}$P]ATP (also at a much higher specific radioactivity than was used to label the internal phosphates), and the 63-nucleotide fragment was dephosphorylated by bacterial alkaline phosphatase. There were 50 times as many moles of dephosphorylated 63-nucleotide fragment present in the reaction as there were moles of phosphorylated 168-nucleotide fragment. After ligation, the RNA was isolated and analyzed by polyacrylamide gel electrophoresis. A band that migrated slightly slower than a MDV-1 (+) RNA marker in the adjacent lane was seen in the autoradiograph of the gel. The RNA in this band was recovered from the gel and a portion was examined by nucleotide sequence analysis. Two oligonucleotides were seen in the fingerprint pattern. One oligonucleotide was in the position expected for $(A)_{10}$U—C—A—C—G, which derived its radioactivity from the phosphate that had been added to the 5' end of the 158-nucleotide fragment. The other oligonucleotide was in the position expected for A—C—A—A—G, which was the 3'-terminal oligonucleotide of the 63-nucleotide fragment, and which could have derived its radioactivity only from the 5'-terminal phosphate that had been added to the 168-nucleotide fragment. Thus, the RNA was the expected 231-nucleotide recombinant formed by the insertion of decaadenylic acid between A—C—A—A—G and U—C—A—C—G in the sequence of MDV-1 (+) RNA: 0.2% of the 168-nucleotide fragments had been ligated to the 63-nucleotide fragment.

(d) Autocatalytic synthesis of the recombinant RNA

The isolated recombinant RNA was used as a template for Qβ replicase. The products were isolated from the reaction and were analyzed by polyacrylamide gel electrophoresis. Two sizes of RNA were seen. The smaller species comigrated with MDV-1 RNA. The larger RNA, which represented 70% of the total, was thus identified as recombinant RNA. Each RNA was eluted from the gel and its complementary (+) and (−) strands were melted apart in 7M urea and isolated by polyacrylamide gel electrophoresis. Each complementary strand of the recombinant RNA migrated more slowly than the corresponding strand of MDV-1 RNA. The presence of both (+) and (−) strands in the recombinant RNA product indicated that its synthesis was autocatalytic. The probable source of the MDV-1 RNA in the Qβ replicase reaction was that some 158-nucleotide fragments had contaminated the 168-nucleotide fragments used during the second ligation, resulting in the presence of MDV-1 (+) RNA in the recombinant RNA template. Subsequenct Qβ replicase reactions were initiated with pure recombinant RNA isolated from the strand-separation gel, and the products of these reactions were not contaminated with MDV-1 RNA.

Fingerprint patterns of strand-separated recombinant RNA were compared with those of MDV-1 RNA to confirm its identity. The only difference seen with [α-$^{32}$P]GTP-labeled (+) strands was that U—C—A—C—G, which was present in MDV-1 (+) RNA, was replaced by $(A)_{10}$U—C—A—C—G in the recombinant (+) RNA. In the complementary (−) strands, labeled with [α-$^{32}$P]UTP to emphasize the heterologous sequence, the only difference seen was that A—C—U—U—G, which was present in MDV-1 (−) RNA, was replaced in the recombinant (−) RNA by a large oligonucleotide that was rich in uridine. Measurement of the radioactivity of the oligonucleotides present in the (−) strand fingerprint patterns indicated that the A—C—U—U—G (whose 3' phosphate was derived from a nearest-neighbor uridine) contained radioactive phosphates from 3 of 33 uridine residues present in MDV-1 (−) RNA, and the large oligonucleotide contained radioactive phosphates from 13 of 43 uridine residues present in the recombinant (−) RNA. The large oligonucleotide of the recombinant (−) RNA was therefore $A(U)_{10}$C—U—U—G, which is complementary to the heterologous sequence inserted into MDV-1 (+) RNA.

Figure 4:
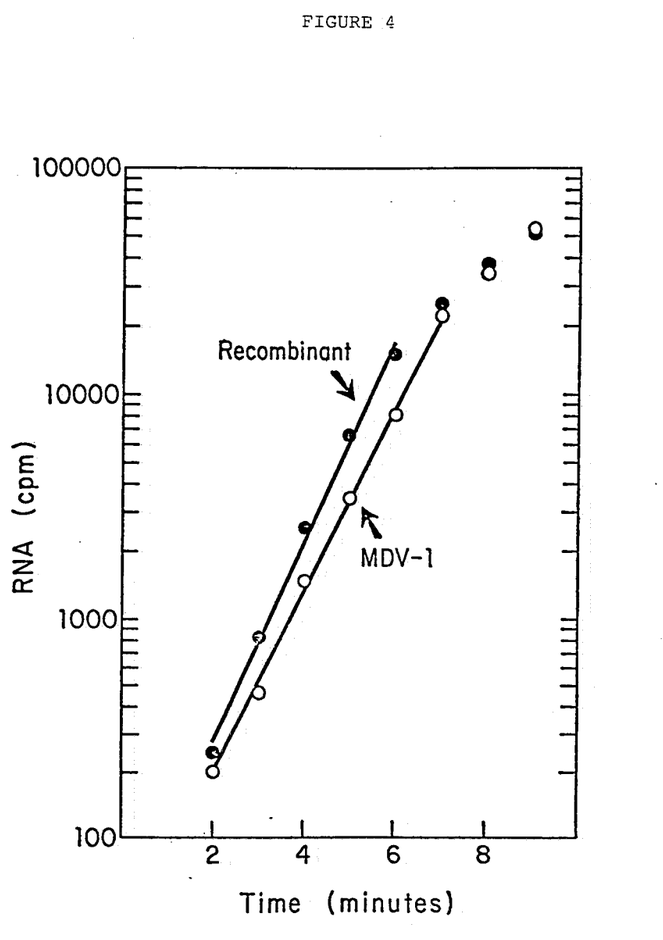

The kinetics of recombinant RNA synthesis were determined by observing two separate Qβ replicase reactions, one employing recombinant RNA as template, and the other employing MDV-1 RNA as template. Before the initiation of synthesis, there was a great excess of Qβ replicase compared with template RNA. Samples were taken from each reaction at one minute intervals and the amount of RNA in each was determined. The amount of RNA present in each reaction increased exponentially with time (see FIG. 4). The rate at which the population of recombinant RNA molecules increased in number was comparable to the rate of increase of the MDV-1 RNA population. Within nine minutes, the number of recombinant RNA molecules increased 300-fold. Thus, the insertion of a heterologous sequence within MDV-1 RNA did not interfere with replication; the mechanism of recombinant RNA synthesis was autocatalytic; and the amount of recombinant RNA increased exponentially.

Discussion

The 231-nucleotide recombinant RNA will be useful as a vehicle for the replication of other RNAs in vitro. In preliminary experiments, we have shown that the recombinant RNA, which contains decaadenylic acid, can be cleaved into two fragments by hybridizing it to decathymidylic acid and then digesting it with ribonuclease H (Donis-Keller, 1979). This is a much simpler method of specifically cleaving MDV-1 (+) RNA. Furthermore, cleavage with ribonuclease H leaves the ends of the fragments in the correct form for ligation (Berkower et al., 1973). This technique will facilitate the construction of recombinants from longer heterologous sequences.

The most important use for these recombinant RNAs will be as templates for the autocatalytic synthesis of large amounts of RNA in vitro. Recombinant RNAs constructed from appropriate sequences would make excellent hybridization probes, since they can be highly labeled and since blotting with RNA instead of DNA results in lower backgrounds. Recombinant RNAs could be made also from unprocessed gene transcripts, which are difficult to obtain. Once constructed, the recombinants would serve as a ready source for the synthesis of additional RNA. These RNAs could then be used as substrates in the isolation of processing enzymes or in studies probing splicing mechanisms (Green et al., 1983). Recombinant RNAs could be made also from eukaryotic mRNAs that are difficult to obtain. Replication of these recombinants in vitro would provide virtually unlimited quantities of mRNAs for use as templates in cell-free translation systems. The presence of the MDV-1 sequences in the template should not affect protein synthesis, since MDV-1 RNA has no AUG codons or ribosome binding sites, and since the initiation and termination signals for translation are located within the mRNA sequence. Thus, recombinant mRNAs might provide a novel means for obtaining useful quantities of rare proteins.

Recombinant RNAs could also be used for the analysis and modification of heterologous sequences. The battery of biological techniques that have been developed to study the synthesis of natural templates by Qβ replicase could be applied to recombinant RNAs. For example, the nucleotide sequence of the inserted RNA could be determined directly by replication of the recombinant in the presence of 3'-deoxyribonucleoside 5'-triphosphate chain terminators (Kramer & Mills, 1978; Mills & Kramer, 1979). Also recombinant RNAs could be prepared from the genomes of viruses and viroids. It would then be possible to select mutants of these heterologous sequences, possessing particular biological properties, through the evolution in vitro of replicating recombinant RNA populations (Mills et al., 1967; Levisohn & Spiegelman, 1969; Kramer et al., 1974). Mutant genomes recovered from these recombinants could then be introduced into cells to study their altered biological activity. Thus, the replication of recombinant RNAs constructed from genomes and gene transcripts should provide a powerful tool for probing and manipulating genetic information.

REFERENCES

Bausch, J. N., Kramer, F. R., Miele, E. A., Dobkin, C. & Mills, D. R. (1983). J. Biol. Chem. 258, 1978–1984.

Berkower, I., Leis, J. & Hurwitz, J. (1973). J. Biol. Chem. 248, 5914–5921.

Casey, J. & Davidson, N. (1977). Nucl. Acids Res. 4, 1539–1552.
Dobkin, C., Mills, D. R., Kramer, F. R. & Spiegelman, S. (1979). Biochemistry, 18, 2038–2044.
Donis-Keller, H., Maxam, A. M. & Gilbert, W. (1977). Nucl. Acids Res. 4, 2527–2538.
Donis-Keller, H. (1979). Nucl. Acids Res. 7, 179–192.
England, T. E. & Uhlenbeck, O. C. (1978). Nature (London), 275, 560–561.
Eoyang, L. & August, J. T. (1971). In Procedures in Nucleic Acid Research (Cantoni, G. L. & Davies, D. R., eds), vol. 2. pp. 829–839, Harper and Row, New York.
Feix, G. (1976). Nature (London), 259, 593–594.
Feix, G. & Hake, H. (1975). Biochem. Biophys. Res. Commun. 65, 503–509.
Green, M. R., Maniatis, T. & Melton, D. A. (1983). Cell, 32, 681–694.
Haruna, I. & Spiegelman, S. (1965a). Proc. Nat. Acad. Sci., U.S.A. 54, 579–587.
Haruna, I. & Spiegelman, S. (1965b). Science, 150, 884–886.
Haruna, I. & Spiegelman, S. (1965c). Proc. Nat. Acad. Sci., U.S.A. 54, 1189–1193.
Kacian, D. L., Mills, D. R., Kramer, F. R. & Spiegelman, S. (1972). Proc. Nat. Acad. Sci., U.S.A. 69, 3038–3042.
Kaufmann, G. & Kallenbach, N. R. (1975). Nature (London), 254, 452–454.
Kaufmann, G. & Littauer, U. Z. (1974). Proc. Nat. Acad. Sci., U.S.A. 71, 3741–3745.
Kramer, F. R. & Mills, D. R. (1978). Proc. Nat. Acad. Sci., U.S.A. 75, 5334–5338.
Kramer, F. R. & Mills, D. R. (1981). Nucl. Acids Res. 9, 5109–5124.
Kramer, F. R., Mills, D. R., Cole, P. E., Nishihara, T. & Spiegelman, S. (1974). J. Mol. Biol. 89, 719–736.
Küppers, B. & Sumper, M. (1975). Proc. Nat. Acad. Sci., U.S.A. 72, 2640–2643.
Levisohn, R. & Spiegelman, S. (1969). Proc. Nat. Acad. Sci., U.S.A. 63, 805–811.
Meyer, F., Weber, H. & Weissmann, C. (1981). J. Mol. Biol. 153, 631–660.
Mills, D. R. & Kramer, F. R. (1979). Proc. Nat. Acad. Sci., U.S.A. 76, 2232–2235.
Mills, D. R., Peterson, R. L. & Spiegelman, S. (1967). Proc. Nat. Acad. Sci., U.S.A. 58, 217–224.
Mills, D. R., Kramer, F. R. & Spiegelman, S. (1973). Science, 180, 916–927.
Mills, D. R., Dobkin, C. & Kramer, F. R. (1978). Cell, 15, 541–550.
Mills, D. R., Kramer, F. R., Dobkin, C., Nishihara, T. & Cole, P. E. (1980) Biochemistry, 19, 228–236.
Nishihara, T., Mills, D. R. & Kramer, F. R. (1983). J. Biochem., 93, 669–674.
Obinata, M., DeLill, S. N. & McCarthy, B. J. (1975). Biochem, Biophys. Res. Commun. 64, 640–647.
Owens, R. A. & Diener, T. O. (1977). Virology, 79, 109–120.
Palmenberg, A. & Kaesberg, P. (1974). Proc. Nat. Acad. Sci., U.S.A. 71, 1371–1375.
Rensing, U. & August, J. T. (1969) Nature (London). 224, 853–856.
Sanger, F., Brownlee, G. G. & Barrell, B. C. (1965), J. Mol. Biol. 13, 373–398.
Sato-Asano, K. (1959). J. Biochem, 46, 31–37.
Schwyzer, M., Billeter, M. A. & Weissmann, C. (1972). Experientia, 28, 750.
Silber, R., Malathi, V. G. & Hurwitz, J. (1972). Proc. Nat. Acad. Sci., U.S.A. 69, 3009–3013.
Spiegelman, S., Pace, N. R., Mills, D. R., Levisohn, R., Eikhom, T. S., Taylor, M. M., Peterson, R. L. & Bishop, D. H. L. (1968). Cold Spring Harbor Symp. Quant. Biol. 33, 101–124.
Tongjian, S. & Meiyan, J. (1982) Scientia Sinica (Series B) 25, 485–495.
Uhlenbeck, O. C. & Cameron, V. (1977). Nucl. Acids Res. 4, 85–98.
Vollenweider, H. J., Koller, T., Weber, H. & Weissmann, C. (1976). J. Mol. Biol. 101., 367–377.
Vournakis, J. N., Carmichael, G. C. & Efstratiadis, A. (1976). Biochem. Biophys. Res. Commun. 70, 744–782.
Walker, G. C., Uhlenbeck, O. C., Bedows, E. & Gumport, R. I. (1975). Proc. Nat. Acad. Sci., U.S.A. 72, 122–126.
Weber, H., Kamen, R., Meyer, F. & Weissmann, C. (1974). Experientia, 30. 711.
Weissmann, C., Feix, G. & Slor, H. (1968). Cold Spring Harbor Symp. Quant. Biol. 33, 83–100.
Zuker, M. & Stiegler, P. (1981). Nucl. Acids. Res. 9, 133–148.

What is claimed is:

1. A recombinant single-stranded RNA molecule, wherein the sequence required for the initiation of product strand synthesis is a cytidine-rich 3' terminal sequence.

2. A recombinant single-stranded RNA molecule as in claim 1 which comprises at least one radiolabeled nucleotide.

3. A recombinant single-stranded RNA molecule as in claim 1, wherein the insertion site for the heterologous sequence of interest is in a loop where viable mutations are known to occur.

4. A recombinant single-stranded RNA molecule as in claim 3, wherein the insertion site is at or near a guanosine residue hypersusceptible to cleavage by ribonuclease $T_1$.

5. A recombinant single-stranded RNA molecule as in claim 1, wherein the MDV-1 RNA is MDV-1 (+) RNA.

6. A recombinant single-stranded RNA molecule as in claim 1, wherein the MDV-1 RNA is MDV-1 (−) RNA.

7. A recombinant single-stranded RNA molecule as in claim 5, wherein the heterologous sequence of interest is inserted between nucleotides 63 and 64.

8. A recombinant single-stranded RNA molecule as in claim 7, wherein the inserted heterologous sequence of interest is decaadenylic acid.

9. A recombinant, single-stranded RNA molecule capable of serving as a template in vitro for the synthesis of a complementary single-stranded RNA molecule by $Q\beta$ replicase which comprises MDV-1 RNA having the structure shown in FIG. 2 or a mutant thereof and a heterologous RNA sequence inserted into the MDV-1 RNA or the mutant thereof essentially without changing the secondary or tertiary structure of the MDV-1 RNA, the heterologous sequence of interest being inserted between two nucleotides, neither of the nucleotides being (a) hydrogen-bonded to any other nucleotide within the MDV-1 RNA, or (b) present within a $Q\beta$ replicase recognition sequence, or (c) present within a sequence for the initiation of product strand synthesis by $Q\beta$ replicase.

* * * * *

UNITED STATES PATENT AND TRADEMARK OFFICE
CERTIFICATE OF CORRECTION

PATENT NO. : 4,786,600

DATED : November 22, 1988

INVENTOR(S) : Fred Russel Kramer, et al.

It is certified that error appears in the above-identified patent and that said Letters Patent is hereby corrected as shown below:

Column 18:

In claim 1, line 26, after "molecule" add --as in claim 1--. Claim "1" should be renumbered claim --9-- and claim "9" should be renumbered claim --1--.

Signed and Sealed this

Fifth Day of November, 1991

Attest:

HARRY F. MANBECK, JR.

Attesting Officer

Commissioner of Patents and Trademarks